(12) United States Patent
Kerslick et al.

(10) Patent No.: US 6,771,737 B2
(45) Date of Patent: Aug. 3, 2004

(54) X-RAY CATHETER WITH MINIATURE EMITTER AND FOCUSING CUP

(75) Inventors: Graham S. Kerslick, Ithica, NY (US); Victor I. Chornenky, Santa Rosa, CA (US); Ali Jaafar, Eden Prairie, MN (US)

(73) Assignee: Medtronic Ave, Inc., Santa Rosa, CA (US)

( * ) Notice: Subject to any disclaimer, the term of this patent is extended or adjusted under 35 U.S.C. 154(b) by 518 days.

(21) Appl. No.: 09/902,659

(22) Filed: Jul. 12, 2001

(65) Prior Publication Data

US 2003/0012339 A1 Jan. 16, 2003

(51) Int. Cl.$^7$ ............................................... H01J 35/00
(52) U.S. Cl. ...................................................... 378/122
(58) Field of Search ........................... 378/122, 65, 119, 378/121, 124

(56) References Cited

U.S. PATENT DOCUMENTS

| | | |
|---|---|---|
| 2,531,583 A | 11/1950 | Ott |
| 3,688,150 A | 8/1972 | Wintzer |
| 3,743,836 A | 7/1973 | Holland et al. |
| 3,875,028 A | 4/1975 | Atlee et al. |
| 3,962,583 A | 6/1976 | Holland et al. |
| 3,979,632 A | 9/1976 | Gunning et al. |
| RE30,082 E | 8/1979 | Atlee et al. |
| 4,288,719 A | 9/1981 | Hernqvist |
| 4,353,006 A | 10/1982 | Schade |

(List continued on next page.)

OTHER PUBLICATIONS

Ward, Roger W., "The Constants of Alpha Quartz," 14$^{th}$ Piezoelectric Devices Conference and Exhibition, Sep. 15–17, 1992, Sponsored by Components Group EIA, 1992, (See especially Table I, pp. 3–4).

U.S. patent application Ser. No. 08/701,764, Chornenky et al., filed Aug. 1996.

U.S. patent application Ser. No. 08/806,244, Chornenky et al., filed Feb. 1997.

U.S. patent application Ser. No. 09/756,287, Chornenky et al., filed Jan. 2001.

Chornenky et al., U.S. app. Ser. No. 09/760,815, "Miniature X–Ray Device and Method of its Manufacture", filed: Jan. 17, 2001.

Sudarshan et al., "The Effect of Chrominum Oxide Coatings on Surface Flashover of Alumina Spacers in Vacuum," IEEE Transactions on Electrical Insulation, vol. EI–11. No. 1, Mar. 1976, pp. 32–35.

Sudarshan et al., "Prebreakdown Processes Associated with Surface Flashover of Solid Insulators in Vacuum," IEEE Transactions on Electrical Insulation, vol., EI–12. No. 3, Jun. 1977, pp. 200–208.

Whetten, N. Ray, "Methods of Experimental Physics" vol. IV, Section 1.1.4, pp. 69–83 (Academic Press 1962).

Primary Examiner—William Oen

(57) ABSTRACT

A cathode for a miniature X-ray device includes an insulating shell, a cathode and an anode. The cathode includes a focusing cup formed into an end. The focusing cup can include a thin metal layer that conforms to an inner surface of the cathode. An emitting material having a low work function, such as diamond, is deposited directly onto the internal surface of the focusing cup. The anode has a flat receiving surface for collecting electrons emitted from the anode. An interior coating is applied as a circumferential belt on the interior surface of the insulating shell. The interior coating, formed of a negative secondary emission yield material, extends lengthwise in the region of the cathode to an anode gap, covering the region of the insulating shell most likely to be subject to stray electrons emitted from the cathode.

20 Claims, 2 Drawing Sheets

U.S. PATENT DOCUMENTS

| | | |
|---|---|---|
| 4,685,118 A | 8/1987 | Furbee et al. |
| 5,007,074 A | 4/1991 | Furbee et al. |
| 5,012,102 A | 4/1991 | Gowlett |
| 5,383,467 A | 1/1995 | Auer et al. |
| 5,582,171 A | 12/1996 | Chornenky et al. |
| 5,713,853 A | 2/1998 | Clark et al. |
| 5,854,822 A | 12/1998 | Chornenky et al. |
| 5,904,670 A | 5/1999 | Schreiner |
| 5,925,016 A | 7/1999 | Chornenky et al. |
| 6,069,938 A | 5/2000 | Chornenky et al. |
| 6,095,966 A | 8/2000 | Chornenky et al. |
| 6,108,402 A | 8/2000 | Chornenky |
| 6,134,300 A | 10/2000 | Trebes et al. |
| 6,148,061 A | 11/2000 | Shefer et al. |
| 6,185,294 B1 | 2/2001 | Chornenky et al. |
| 6,275,566 B1 | 8/2001 | Smith et al. |
| 6,280,413 B1 | 8/2001 | Clark et al. |
| 6,289,079 B1 | 9/2001 | Chornenky et al. |
| 6,424,696 B1 * | 7/2002 | Chin ..................... 378/101 |
| 6,477,235 B2 * | 11/2002 | Chornenky et al. ......... 378/143 |
| 6,546,077 B2 * | 4/2003 | Chornenky et al. ......... 378/122 |

* cited by examiner

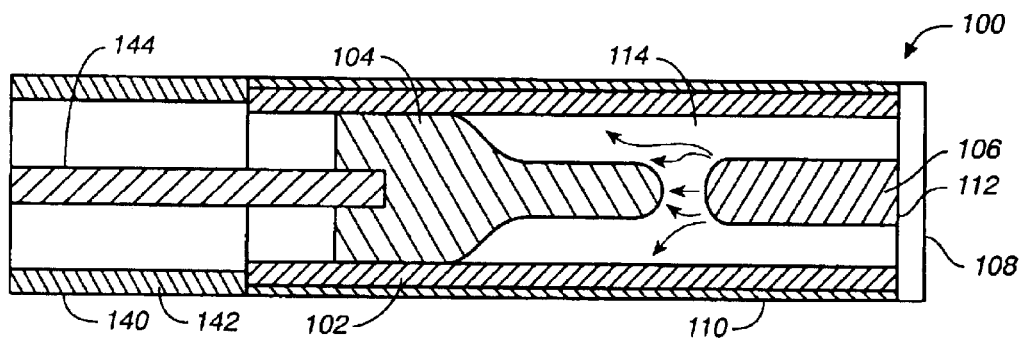
FIG._1
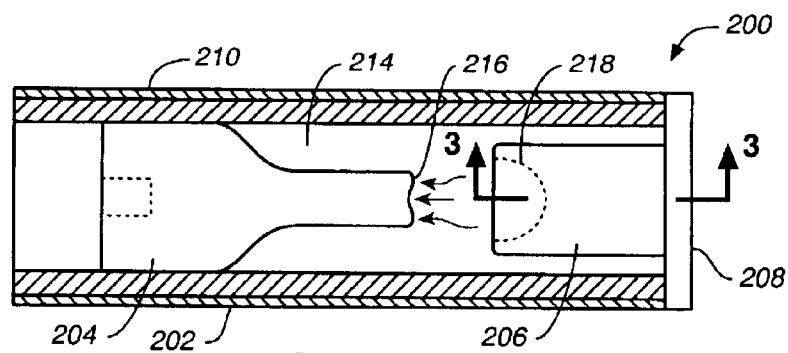
FIG._2
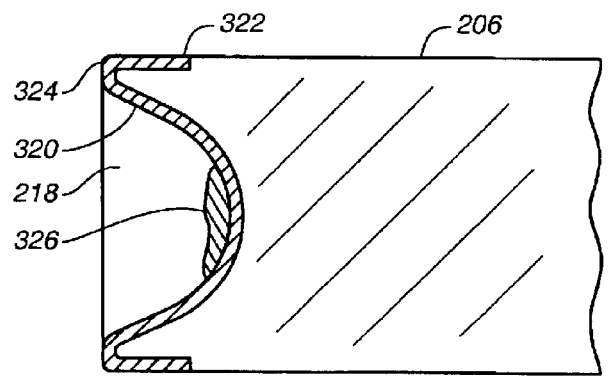
FIG._3

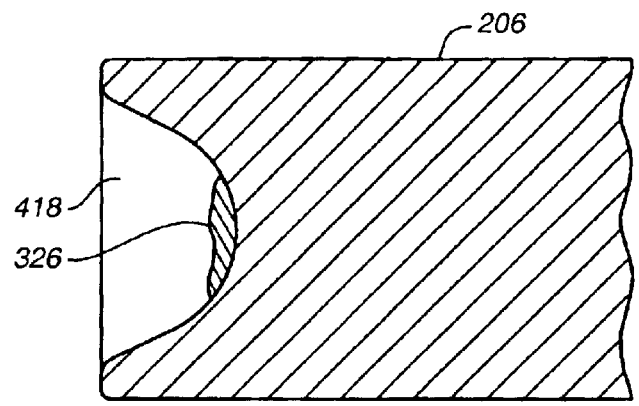
FIG._4
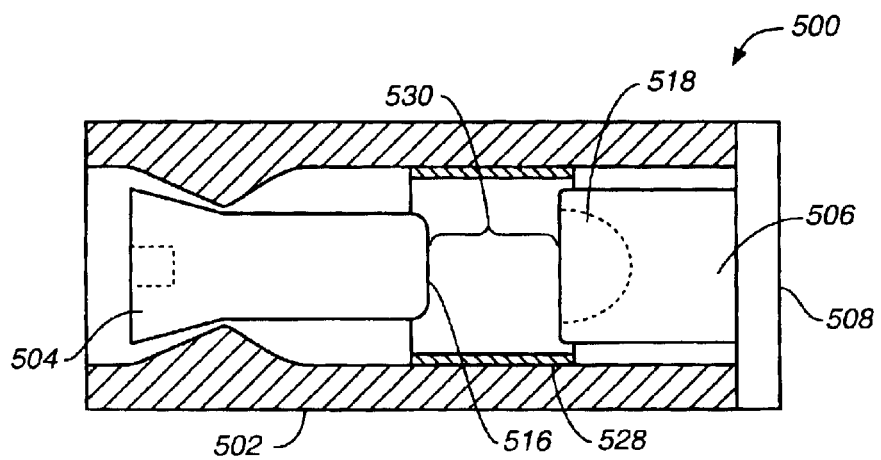
FIG._5
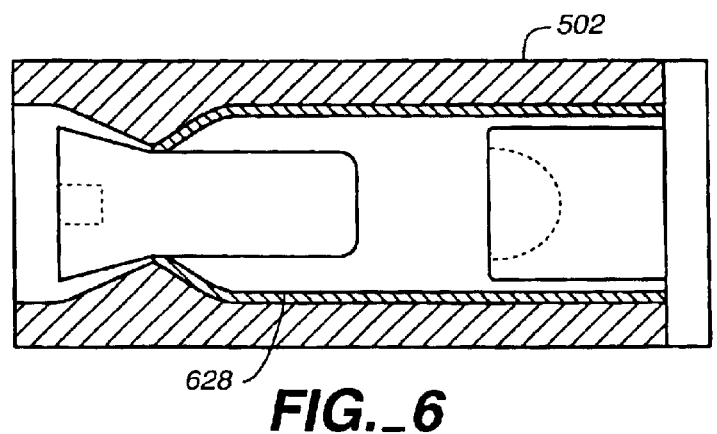
FIG._6

X-RAY CATHETER WITH MINIATURE EMITTER AND FOCUSING CUP

BACKGROUND OF THE INVENTION

1. Field of the Invention

The present invention relates generally to a miniature X-ray device. More specifically, the present invention relates to an X-ray device for a catheter. More specifically, the present invention relates to an X-ray device having a focusing cup containing an electron emitter material.

2. Background Art

Cardiovascular diseases affect millions of people, often causing heart attacks and death. One common aspect of many cardiovascular diseases is stenosis, or the thickening of an artery or vein wall, decreasing blood flow through the vessel. Angioplasty procedures have been developed to reopen clogged arteries without resorting to a bypass operation. However, in a large percentage of cases, arteries become occluded again after an angioplasty procedure. This recurrent thickening of the vessel wall is known as restenosis. Restenosis frequently requires a second angioplasty and eventual bypass surgery. Bypass surgery is very stressful on the patient, requiring the chest to be opened, and presents risks from infection, anesthesia, and heart failure.

One method of treating restenosis includes using miniature X-ray devices to irradiate blood vessels and other human body cavities. An X-ray catheter is comprised of a coaxial cable and a miniature X-ray emitter connected to the cable's distal end. The proximal end of the coaxial cable is connected to a high voltage power source. The X-ray emitter consists of an anode and a cathode assembly mounted in a miniature shell (tube), made of an insulator with very high dielectric strength. Typically, the anode is comprised of platinum, tungsten, or another heavy metal.

To activate the emitter, high voltage is applied between electrodes. A high electric field is generated at the cathode surface and causes field emission of electrons. Emitted electrons are accelerated by the electric field and impinge on the anode. As the electrons strike the anode, X-ray energy is produced and radiated. The radiation occurs as high-speed electrons are slowed or stopped by passing near the positively charged nuclei of the anode material, or, as incoming electrons collide with anode atoms, knocking the electrons near the anode atom nuclei out of orbit and replacing the knocked out electrons with other electrons.

For coronary applications, the outer diameter of an X-ray emitter must be as small as 1.00 to 1.25 mm. The close proximity of each component of the emitter makes it difficult to control with preciseness the direction of flow of emitted electrons. A fraction of electrons emitted by the cathode may hit the inner wall of the insulating shell. The inner surface of the shell has an electric field parallel to its surface that is capable of creating an electron avalanche along the inner surface. By knocking electrons from the wall, the avalanche causes positive charging of the surface which distorts the electric field near the cathode, causing even more electrons to be emitted to the wall.

An electron avalanche also increases leakage current. Leakage current is electron flow that passes from the cathode to any portion of the emitter other than the anode. When electrons collide with the interior wall of the insulating shell, the electrons provide a path for leakage current along the wall between the cathode and the anode. This leakage current can be hundreds of times as high as the initial field emission current onto the wall. Leakage current does not produce X-rays but causes undesired heating of the emitter.

Additionally, leakage current affects the proper monitoring and calculation of the irradiation dose. Irradiation dose is calculated on the basis of the emitter's current. As leakage current increases, the amount of X-ray radiation decreases with no change in the measured current. Thus, the measurement of irradiation dose becomes inaccurate and guesswork.

Secondary electron emission (SEE) ratio (or yield) is the number of secondary electrons emitted on the average per incident primary electron. SEE yield δ depends on the energy of the incident electrons. For most insulating materials, and in the range of energy between ten and several hundreds of electron-volts, δ can have a value of about 1 to 5. These insulating materials support electron avalanches at their surfaces which result in positive charging of the wall. However, some materials have an SEE yield less than 1. Accordingly, electron bombardment causes negative charging of the surface and subsequent repelling of the incident electrons, eliminating electron impact to the wall.

What is needed is a miniature X-ray device for an X-ray catheter having a lower incidence of electron avalanche and leakage current.

BRIEF SUMMARY OF THE INVENTION

The present invention is a miniature X-ray emission device having an insulating shell that houses a cathode and an anode. The cathode includes a focusing cup formed into one end. The focusing cup is an axially symmetrically hollow that provides a converging electron beam toward the anode. The anode has a flat surface for collecting electrons emitted from the anode. The flat surface aids in achieving a more uniform azimuthal distribution of this radiated X-ray energy.

The focusing cup can include a thin metal layer that conforms to an inner surface of the cathode. Such a coating avoids the problem of field emission from the edge of the anode, which may be located in moderately close proximity to the wall of the insulating shell. The metal layer is a non-emitting metal of high work function. The depth of the focusing cup is selected such that it is within an area having an electric field in the range of 3–5 times lower than the electric field at the edge of the focusing cup.

An emitting material having a low work function is deposited directly onto the internal surface of the focusing cup. A preferred emitting material is a carbon product, such as graphite or diamond. Diamond is a low work function material having a negative electron affinity. When diamond is used as the emitting material, the emitting product should be a thin layer or film to allow diamond electrons to be properly replenished from the rear of the emitting material, through the anode. The thin layer can be accomplished through laser deposition of the emitting material. A graphite mixture may be used to provide increased electron replenishment over diamond.

An interior coating can be applied as a circumferential belt on the interior surface of the insulating shell. The interior coating extends lengthwise in the region of the cathode to an anode gap, covering the region of the insulating shell most likely to be subject to stray electrons emitted from the cathode. The interior coating is formed of a negative secondary emission yield material, such as chromium oxide or titanium. The interior coating can also be applied to the whole length of the interior surface of the insulating shell.

BRIEF DESCRIPTION OF THE DRAWINGS

The foregoing and other features and advantages of the invention will be apparent from the following, more particular description of a preferred embodiment of the invention, as illustrated in the accompanying drawings.

FIG. 1 is a cross-sectional view of an embodiment of a conventional miniature X-ray emitter.

FIG. 2 is a partial cross-sectional view of an embodiment of the X-ray emitter of the present invention.

FIG. 3 is a cross-section taken along a line 3—3 of FIG. 2 of the cathode of the present invention.

FIG. 4 is a cross-section taken along a line 3—3 of FIG. 2 showing another embodiment of the cathode of the present invention.

FIG. 5 shows a partial cross-sectional view of an embodiment of the circumferential coating of the X-ray emitter of the present invention.

FIG. 6 shows a partial cross-sectional view of an alternate embodiment of an X-ray emitter of the present invention.

DETAILED DESCRIPTION OF THE INVENTION

The preferred embodiment of the present invention is now described with reference to the figures where like reference numbers indicate identical or functionally similar elements. While the invention is described in terms of a specific embodiment, it should be understood that this is done for illustrative purposes only. A person skilled in the relevant art will recognize that various modifications, rearrangements and substitutions can be made without departing from the spirit of the invention.

FIG. 1 shows a standard miniature X-ray emitter generally at 100. X-ray emitter 100 is to be introduced to a patient's blood vessels or other cavities via a trocar or introducer. X-ray emitter 100 comprises an insulating shell 102, an anode 104, a cathode 106 and a cathode cap 108. An interior space 114 is kept as a substantially vacuum environment.

Cathode cap 108 is electrically connected to cathode 106 at cathode bond 112, providing an electrical contact between cathode cap 108 and cathode 106. Cathode bond could be a brazed joint of a conductive material, such as a metal or metal alloy or other similar bond, as would be apparent to one skilled in the relevant art. Insulating shell 102 is coated with a conductive metal coating 110, which provides electrical contact between cathode cap 108 and a coaxial cable 140.

High voltage is applied through a braided portion 142 of coaxial cable 140 to metal coating 110. The current travels from metal coating 110 through the electrically connected cathode cap 108 to cathode 106. The applied voltage causes an electric field to generate around cathode 106, causing cathode 106 to emit electrons, which travel through the vacuum of interior space 114 toward anode 104. As the electrons approach the anode, they are deflected by the positively charged nuclei of the anode material, losing energy and radiating X-rays. Anode 104 is electrically connected to an interior wire 144 of coaxial cable 140, thereby completing a circuit.

As shown in FIG. 1, both anode 104 and cathode 106 have rounded ends within interior space 114. As the rounded end of cathode 106 emits electrons, a fraction of the electrons are emitted at relatively high angles to the emitter axes and impinge on the inner surface of the insulating shell. This fraction creates the electron avalanche and associated current leakage described above.

Outside the patient's body the cable is secured to a pullback device, which can be used to pull the cable to move emitter 100 along the blood vessel or the body cavity to provide irradiation for a predetermined length.

Typically, an X-ray emitter is introduced to a patient's vasculature through a guiding catheter. The guiding catheter is typically a hollow, tubular catheter of one or more pieces having a distal end and a proximal end. The guiding catheter is maneuvered through the patient's vasculature with the use of a flexible guidewire having a diameter of approximately 0.010 to 0.018 inches and a length of about 180 centimeters. The distal end of the guidewire is extremely flexible so that it may be routed through the convoluted arterial pathway to the target area. After the distal portion of the guidewire is positioned at the target area, the distal end of the guiding catheter is placed over the proximal end of the guidwire. The guiding catheter is advanced along the guidewire, through the patient's vasculature until the distal end is positioned near the target area.

The guidewire is then withdrawn from the guiding catheter, leaving the guiding catheter within the vasculature, and the X-ray emitter and coaxial cable are introduced through the guiding catheter to the target site. The X-ray emitter is advanced by the operating physician or by a mechanism attached to the cable outside of the patient's body.

FIG. 2 shows a miniature X-ray emitter 200 of the present invention. X-ray emitter 200 includes an insulating shell 202. Insulating shell 202 can be comprised of any material having a very high dielectric strength (104–200 kV/mm) combined with high electrical resistivity ($10^{15}$ Ohm-cm), gas impermeability, and moderate mechanical strength. Material for insulating shell 102 has a low to moderate absorption of X-ray within the energy range of 10–20 kV. Thus, the material should be composed of relatively low weight elements. Crystalline quartz and diamond both meet these requirements, and are good materials for the insulating shell. X-ray emitter could be the emitter disclosed in co-pending U.S. application Ser. No. 09/760,815, filed Jan. 17, 2001, which is incorporated in its entirety by reference herein.

An anode 204 is housed within insulating shell 202. Anode 202 is the electron-collecting electrode of X-ray emitter 200. The anode is preferably tungsten, however, platinum, gold or other heavy metals are also good materials for the anode. As seen in FIG. 2, an interior end of anode 204 is a flat surface 216. Flat surface 216 aids in achieving a more uniform azimuthal distribution of the radiated X-ray energy. This reduces the incidence of X-ray shadow that may occur whenever there is a linear shift in the electron beam from the center of an anode having a semispherical interior end.

A cathode 206 is also housed within insulating shell 202. Cathode 206 is the negatively-charged electrode of emitter 200. A cathode cap 208 is bonded to cathode 206 using any bonding method known to one skilled in the relevant art, thereby connecting cathode 206 to insulating shell 202. A focusing cup 218 is formed in an end of cathode 206. Focusing cup 218 is an axially symmetric hollow provided at the tip of cathode 206. An interior space 214 separates cathode 206 from anode 204 in X-ray emitter 200.

Interior space 114 is kept at a substantially vacuum environment. In one embodiment, getter material is incorporated into the material of cathode 206, such that cathode 206 directly absorbs gas molecules from the interior space.

Insulating shell 202 is coated with a metal coating 210 which provides electrical contact between cathode cap 208 and the braid of a coaxial cable (not shown). Metal coating 210 may be any non-corrosive, conductive metal, such as silver or titanium. In one embodiment, metal coating 210 is comprised of the same material as cathode 206. Other metals or metal alloys could be used, as would be apparent to one skilled in the relevant art. In a preferred embodiment, the metal is sputtered onto emitter 200 to provide a 1–5 micron thick layer of metal, however, the layer could be more or less thick, as would be apparent to one skilled in the relevant art.

The metal coating 210 on the outer surface of emitter 200 performs several important functions such as: providing a path for the operating current; providing electrical safety for the patient; shielding the triple point of the emitter thereby increasing its hold off voltage; and focusing the electron beam along the axis of the emitter, to prevent charging the inside wall of the insulating shell and discharges associated with it.

FIG. 3 provides a cross-sectional view of cathode 206 taken along a line 3—3 of FIG. 2. Focusing cup 218 is an axially symmetric hollow formed into the tip of cathode 206. The curved surface of focusing cup 218 focuses emitting electrons into a converging, rather than diverging, electron beam, bombarding the central part of the anode tip, as denoted by the arrows in FIG. 2. Accordingly, electron emission toward the interior wall of the insulating shell is greatly reduced or eliminated.

Focusing cup 218 includes a metal layer 320. Metal layer 320 is a thin layer that conforms to an inner surface of cathode 206. Metal layer 320 extends from the interior surface of focusing cup 218, around the focusing cup edge 324 and extends along the side of cathode 206, terminating at a point a distance from the cup edge, as shown at 322. Such a coating avoids the problem of field emission from the anode from focusing cup edge 324, which may be located in moderately close proximity to the wall of the insulating shell.

Metal layer 320 and cathode 206 can be formed separately with metal layer 320 being placed in a hollow formed into the end of cathode 206 or, alternatively, cathode 206 can be formed around metal layer 320, as would be apparent to one skilled in the relevant art. Although in the preferred embodiment of the invention, metal layer 320 covers the complete concave surface of focusing cup 218 and extends down a side of cathode 206, metal layer 320 need not extend around the edge of focusing cup 218 and extend down the side, but could cover only the concave surface. Likewise, metal layer 320 need not cover the entire concave surface, and may cover only a partial surface.

Metal layer 320 is a non-emitting metal of high work function, such as platinum, titanium or gold. Work function is measured by the amount of energy required to displace an electron from the elemental atom. Accordingly, metal layer 320 is chosen such that electrons are not easily emitted from metal layer 320 to reduce the incidence of electrons emitted from focusing cup 218. In a preferred embodiment, metal layer is sputtered onto cathode 206 using a standard sputtering device, as would be apparent to one skilled in the relevant art.

In the preferred embodiment, the depth of the focusing cup is selected such that it is within an area having an electric field in the range of 3–5 times lower than the electric field at the focusing cup edge 324. An emitting material 326 having a low work function is deposited directly onto metal layer 320, preferably at the apex of focusing cup 218. However, emitting material 326 could be deposited on any area of focusing cup 218. Although the electric field is less at the region of the emitting material 326 than at focusing cup edge 324, emitting material 326 is selected such that it can emit a sufficient number of electrons, even in the low field, to produce sufficient X-ray energy in the X-ray device.

A preferred emitting material is a carbon product, such as graphite or diamond product. Diamond product includes diamond, graphite and mixtures including either of these. Diamond is a low work function material having a negative electron affinity. Accordingly, in a vacuum, diamond emits electrons spontaneously. This result is achieved because diamond electrons have a higher energy than that of the vacuum. When diamond is used as emitting material 326, the emitting product should be a thin layer or film to allow diamond electrons to be properly replenished from the rear of the emitting material, through anode 206. In one embodiment, emitter material 326 is comprised of a carbon mixture having about 30% graphite type bonding and about 70% diamond type bonding. Emitting material could have a thickness in the range of 0.01–5 microns. In a preferred embodiment, emitting material 326 should have a thickness between 0.1–2.0 microns, and more preferably about 1 micron. The thin layer can be accomplished through laser deposition of the emitting material.

Use of a carbon product, such as diamond or graphite, maintains other advantages as well. For instance, in a standard X-ray emitting device, one way of providing energy to the emitting material, and thereby causing electron emission, is by increasing the temperature of the cathode. In an X-ray catheter, excessive heating is undesirable as it can cause discomfort or injury to the patient. Use of a carbon product, such as diamond or graphite having a negative electron affinity, allows electron emission to occur within a vacuum environment without applying heat. Energy is provided to the emitting material through the cathode to replenish electrons and to control the rate of electron emission by increasing or decreasing the power supplied, but the energy is not required to be in levels that would allow it to be converted to heat.

Likewise, the use of a carbon product, such as diamond or graphite as the emitting material, deposited directly on the cathode or the metal layer surface, eliminates the need for circuitry and leads extending through the cathode. The cathode itself carries the current to the emitting material. Accordingly, an X-ray catheter device can be more easily manufactured to meet the size requirements defined by the size of a typical patient's vessels.

FIG. 4 shows another embodiment of a cross-sectional view of cathode 206 taken along line 3—3 of FIG. 2. As shown in FIG. 4, emitting material 326 is deposited directly on a surface of focusing cup 418 formed into an end of a cathode 206. As described above, emitting material 326 is a carbon product, such as diamond or graphite. In this embodiment, cathode 206 does not include a metal layer having high work function. Accordingly, emitting material 326 is deposited directly on the surface of cathode 206, preferably in the apex of focusing cup 418. However, emitting material could be deposited at any location within focusing cup 418. In this embodiment, cathode 206 can be completely comprised of a high work function material that serves as a conductor for conducting electrical current to emitting material 326. Additionally, cathode 206 could be comprised of a metal alloy of getter material, thereby serving the dual purpose of maintaining a vacuum environment within an insulating shell and conducting electrical current to emitting material 326.

FIG. 5 shows an X-ray emitter 500 having an interior coating 528 applied to the inner surface of an insulating shell 502. X-ray emitter 500 includes an anode 504, a cathode 506 and a cathode cap 508. In this embodiment, insulating shell 502 and anode 504 connect at conical surfaces that are bonded together, preferably by brazing, as would be apparent to one skilled in the relevant art. Cathode 506 is shown as having a focusing cup 518 as described in any of the above embodiments. Likewise, anode 504 is shown as having a flat surface 516 as was described in the previous embodiments. However, it would be apparent to one skilled in the relevant art that cathode 506 and anode 504, used with X-ray emitter 500 having interior coating 528, could each have rounded ends as was described above with reference to FIG. 1.

Interior coating 528 is a circumferential belt on the interior surface of insulating shell 502. Interior coating 528 extends lengthwise in the region of the cathode to anode gap 530. This covers the region of insulating shell 502 most likely to be subject to stray electrons emitted from cathode 506. Interior coating 528 is formed of a negative secondary emission yield material. Accordingly, when an electron is emitted from cathode 506, and instead of being directed at anode 504, is directed toward insulating shell 502 and arrives at interior coating 528, the electron will be absorbed into interior coating. With more electrons arriving at interior coating 528 than leaving coating 528, a negative charge is developed. Accordingly, interior coating 528 will begin to repel any additional electrons from the surface of insulating shell, thereby avoiding electron avalanche and leakage current. The absence of any appreciable positive charge on the insulating shell surface minimizes the prevalence of stray electrons arriving at the insulating shell surface, and discourages the positive charging and leakage that would result therefrom. Furthermore, by increasing the negative charge of the interior coating 528, the electron beam remains convergent toward anode 504 increasing efficiency of the system.

One suitable material for interior coating 528 is chromium oxide ($Cr_2O_3$). $Cr_2O_3$ has an SEE yield of 0.9 and a relatively high surface resistivity of about $10^{10}$ Ohms/square. Any material having an SEE yield below 1.0 could be used as interior coating 528. In one embodiment, interior coating 528 is a titanium coating. Titanium has an SEE yield of 0.9. However, titanium has a high conductivity. Therefore, when using titanium as interior coating 528, it is important that coating 528 does not extend to another conductor, such as anode 504 or cathode 506 because the titanium could assist in causing leakage current.

In a preferred embodiment, interior coating 528 is about 30 to 1000 angstroms thick. However, interior coating could be thicker or thinner as would be apparent to one skilled in the relevant art.

FIG. 6 shows the embodiment of FIG. 5 having an interior coating 628 that extends substantially the entire length of the interior surface of insulating shell 502. By covering substantially the entire length of the interior surface of insulating shell 502, the chance of electrons bombarding the wall of insulating shell 502 is greatly reduced. $Cr_2O_3$ should be used as the material of interior coating 628. Because of its high resistivity, $Cr_2O_3$ does not easily conduct and will not result in an electron avalanche or high leakage current. However, anytime a coating is connected to the electrodes, at least a very low leakage current is expected.

If interior coating 528 is $Cr_2O_3$, then coating 528 is applied by soaking insulating shell 502 in a chromium trioxide and water solution mixed in a 1:1 ratio. After soaking, insulating shell 502 is fired at a temperature of about 900 degrees C. for several hours. Another method of applying $Cr_2O_3$ is to deposit metallic chromium into insulating shell 502 and oxidizing the chromium to form $Cr_2O_3$. Masking can be used to cover areas of insulating shell 502 that do not require an interior coating.

While the invention has been particularly shown and described with reference to preferred embodiments thereof, it will be understood by those skilled in the art that various changes in form and detail may be made therein without departing from the spirit and scope of the invention.

What is claimed is:

1. A miniature X-ray device for an X-ray catheter comprising:
    an insulating shell having an interior space at a substantially vacuum environment;
    an anode disposed within said insulating shell;
    a cathode disposed within said insulating shell, opposite said anode, said cathode having a focusing cup formed therein; and
    an emitter material disposed on said focusing cup.
2. The X-ray device of claim 1, wherein said emitter material is a diamond product.
3. The X-ray device of claim 2, wherein said emitter material is deposited by laser deposition.
4. The X-ray device of claim 1, wherein said focusing cup comprises a metal coating on a surface of said focusing cup.
5. The X-ray device of claim 4, wherein said emitter material is a diamond product.
6. The X-ray device of claim 4, wherein said metal coating is a high work function metal.
7. The X-ray device of claim 1, wherein a vertex of said focusing cup is located in a region where the resulting electric field is 3 to 5 times lower than the electric field at an edge of said focusing cup.
8. The X-ray device of claim 1, wherein an end of said anode is a flat surface.
9. A miniature X-ray device for an X-ray catheter comprising:
    an insulating shell having an interior space at a substantially vacuum environment;
    an anode disposed within said insulating shell;
    a cathode disposed within said insulating shell, opposite said anode; and
    a coating having a negative secondary emission yield disposed on a surface of said insulating shell.
10. The X-ray device of claim 9, wherein said coating is applied to an interior surface of said insulating shell.
11. The X-ray device of claim 10, wherein said coating is applied in a circumferential band in the region of a gap between said cathode and said anode.
12. The X-ray device of claim 11, wherein said coating is selected from the group of chromium oxide and titanium.
13. The X-ray device of claim 9, further comprising:
    a focusing cup formed in said cathode; and
    an emitter material disposed on said focusing cup.
14. The X-ray device of claim 13, wherein said emitter material is a diamond product.
15. The X-ray device of claim 14, wherein said emitter material is deposited by laser deposition.
16. The X-ray device of claim 9, wherein said coating is 0.1–2.0 microns thick.
17. A miniature X-ray device for an X-ray catheter comprising:
    an insulating shell having an interior space at a substantially vacuum environment;

an anode disposed within said insulating shell;

a cathode disposed within said insulating shell, opposite said anode, said cathode having a focusing cup formed therein, said cup including a non-emitting metal liner;

an emitter material disposed directly on a surface of said focusing cup; and a coating having a negative secondary emission yield disposed on a surface of said insulating shell.

18. The X-ray device of claim 17, wherein said emitter material is a diamond material.

19. The X-ray device of claim 18, wherein said emitter material is deposited by laser deposition.

20. The X-ray device of claim 16, wherein a tip of said anode is flat.

* * * * *